(12) United States Patent
Luttich

(10) Patent No.: US 8,251,993 B2
(45) Date of Patent: Aug. 28, 2012

(54) METHOD AND DEVICE FOR LESS INVASIVE SURGICAL PROCEDURES ON ANIMALS

(76) Inventor: Edward Luttich, Fallbrook, CA (US)

( * ) Notice: Subject to any disclaimer, the term of this patent is extended or adjusted under 35 U.S.C. 154(b) by 641 days.

(21) Appl. No.: 12/359,307

(22) Filed: Jan. 24, 2009

(65) Prior Publication Data

US 2009/0192507 A1  Jul. 30, 2009

Related U.S. Application Data

(60) Provisional application No. 61/023,797, filed on Jan. 25, 2008, provisional application No. 61/023,795, filed on Jan. 25, 2008, provisional application No. 61/118,838, filed on Dec. 1, 2008.

(51) Int. Cl.
*A61B 18/18* (2006.01)
(52) U.S. Cl. .......................................................... 606/41
(58) Field of Classification Search .................. 604/22, 604/158; 606/27–29, 31, 39, 41, 110, 111; 607/96, 101, 102, 134, 135, 154
See application file for complete search history.

(56) References Cited

U.S. PATENT DOCUMENTS

| 5,413,575 | A | 5/1995 | Haenggi |
| 5,536,267 | A | 7/1996 | Edwards et al. |
| 5,868,140 | A | 2/1999 | Miller et al. |
| 6,102,907 | A | 8/2000 | Smethers et al. |
| 6,210,355 | B1 * | 4/2001 | Edwards et al. ............... 604/22 |
| 6,682,501 | B1 * | 1/2004 | Nelson et al. ................. 604/22 |

OTHER PUBLICATIONS

International Search Report and Written Opinion from PCT/US2009/031928 issued Jun. 22, 2009.

* cited by examiner

*Primary Examiner* — Manuel Mendez
(74) *Attorney, Agent, or Firm* — Eleanor M. Musick; Procopio, Cory, Hargreaves & Savitch LLP

(57) ABSTRACT

The present invention is directed to a method and system for less invasive surgical procedures on animals. In accordance with various embodiments, electromagnetic energy is applied in a controlled application and projected into the tissue of an animal. The controlled application of the electromagnetic energy heats the targeted tissue causing cell necrosis, collagen shrinkage or scar tissue production, often without requiring a surgical incision.

24 Claims, 9 Drawing Sheets

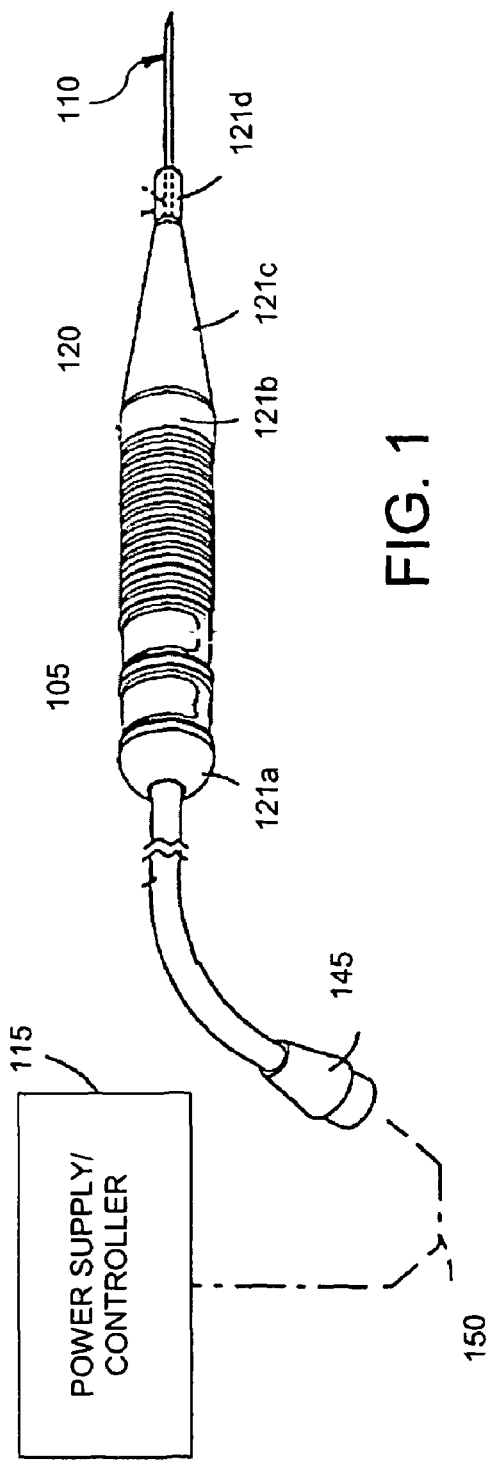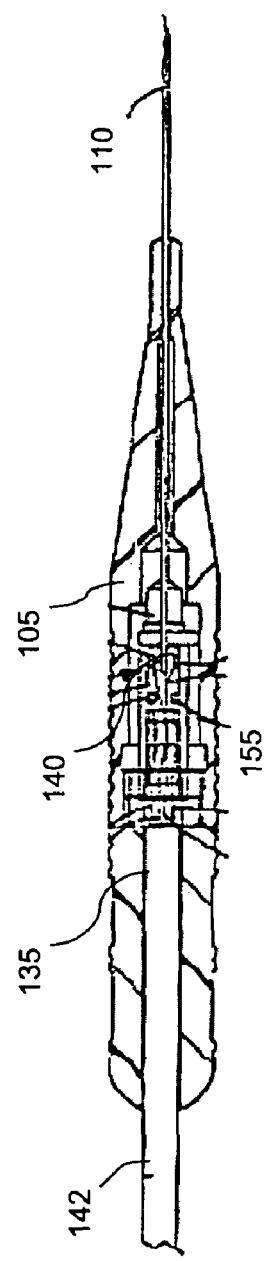

METHOD AND DEVICE FOR LESS INVASIVE SURGICAL PROCEDURES ON ANIMALS

RELATED APPLICATIONS

This application claims the priority of U.S. Provisional Applications No. 61/023,797 and 61/023,795, both filed Jan. 25, 2008, and U.S. Provisional Application No. 61/118,838, filed Dec. 1, 2008, each of which is incorporated herein by reference in its entirety.

FIELD OF THE INVENTION

The present invention relates generally to a device and methods for performing less invasive surgical procedures on animals using focused energy.

BACKGROUND OF THE INVENTION

Basic instincts drive most animals to produce offspring in numbers limited only by the animal's biological capacity and environmental conditions, e.g., breeding season, gestation period and competition. These instincts are clearly problematic for domesticated animals for which natural controls, such as food supply, are no longer a factor. For example, dogs and cats have the ability to produce so many offspring that, if unchecked, it would become a significant burden on society. Current statistics indicate that tens of thousands of unwanted companion animals are euthanized in the U.S. every year. Other unwanted dogs and cats become feral, potentially endangering wildlife, livestock and, on occasion, humans.

The most common solution is to promote and implement widespread neutering and spaying of domesticated animals. For neutering of male animals, the most frequently used technique consists of placing the animal under general anesthesia, creating an incision in or near the scrotum, exteriorizing each testicle through the incision, cutting the spermatic cord and ligaments to remove the testicle, and, for dogs, suturing the incision.

While neutering is generally considered a minor surgical procedure, it nonetheless requires general anesthesia, and there can be complications if the surgical area becomes infected. Further, incomplete ligation of the spermatic cord can lead to post-operative bleeding. Many pet owners form a strong emotional bond with their animals, and some may feel the current technique for neutering animals is cruel, overly invasive, and painful. It would be desirable to provide a method for neutering an animal in a less invasive manner that can be considered less cruel and painful. With such an improved technique, the pet owner would be able to do what is beneficial for society, without the concern that they have harmed a beloved pet.

Most animals vocalize as a form of communication. For example, a dog will bark at other dogs, when a visitor at the door is perceived as an intruder, or when an actual intruder is detected within its territory. Dogs may bark incessantly when they do not receive appropriate physical activity, or when they are bored, anxious or frustrated. Some dogs, such as those with separation anxiety, will bark incessantly when left alone, while others bark at the slightest noise, which can annoy its owners and/or owners' neighbors, particularly when the dog barks late at night or early in the morning when people are sleeping. Municipalities often have noise ordinances that can impose fines or other sanctions for nuisance barking if repeated complaints are filed. When a barking dog becomes a nuisance, the owners may be forced into the decision of either finding a way to silence the dog or getting rid of it. For a particularly problematic barker, behavior modification or devices such as bark collars or ultrasonic bark deterrents may not be sufficient.

As a last resort to deal with a loud and persistently barking dog, a surgical procedure can be performed on the animal to reduce the volume of the bark by essentially removing or disabling the vocal chords. The vocal cords are cut or cauterized, leaving the animal mute or severely reducing the physical ability of the animal to make noise. There are two ways to perform this procedure: one method goes through the animal's mouth. This approach is simpler and quicker. The other method goes through the dog's larynx, or voice box. The second method is more expensive and a little more difficult, but is better because the veterinarian can suture the lining of the airway back together to keep scar tissue from developing and blocking the dog's airway. Surgical methods have been characterized as cruel, overly invasive, and physically painful for the animal. Complications can occur, including growth of scar tissue that can block the airway or cause a strange sounding bark. It is not unusual for subsequent surgeries to be required to correct a previous procedure that did not work. Accordingly, the need remains for a means for reducing noise made by the animal in a less invasive manner.

Numerous other surgical procedures on animals would benefit from less invasive methods. Such procedures include, but are not limited to: 1) correction of slipping kneecaps in small dogs; 2) treatment of braceocephallic syndrome in flat-faced dog breeds; 3) treatment of collapsing trachea in dogs and horses; 4) treatment of laryngeal paralysis in large dog breeds and horses; 5) removal of fatty tumors in dogs; 6) treatment of posterior heel pain in horses; 7) repair of suspensory ligaments and flexor tendons in horses; 8) spaying of female animals; and 9) treatment of hyperthyroidism.

BRIEF SUMMARY OF THE INVENTION

The present invention is directed to a device and methods for performing less invasive surgical procedures on animals. In accordance with various embodiments, electromagnetic energy is applied in a controlled application and projected into the living tissue of an animal. The controlled application of the electromagnetic energy causes controlled heating of the living tissue beneath the surface. The heating of the living tissue beneath the surface causes one or more of cell necrosis, scarring and collagen shrinkage, based upon the specific heating conditions and the nature of the tissue, thus modifying the living tissues without a surgical incision.

The general advantages of the present invention include reduced trauma and bleeding, less pain, speed, ease and effectiveness of the procedure, the possibility of using local anesthesia, plus sedation, if needed, instead of general anesthesia, quicker post procedure recovery, reduced possibility of infection, less impact on external appearance, and reduced overall cost versus current surgical techniques.

According to one embodiment, the application of the electromagnetic energy induces heating of living tissue structures to kill cells, create scar tissue or shrink collagen in place of traditional surgical techniques. The electromagnetic energy can be delivered in several different ways. Energy in the radio-frequency (RF) range (around 460 kHz), which is most commonly used, can be delivered by either one or more tissue penetrating needle probes or by a surface probe.

A particular organ or tissue structure has a characteristic thermal mass which determines how much energy is required to raise the tissue temperature to a pre-determined level and the rate of thermal dissipation, which determines how quickly the structure loses energy to its surroundings as the temperature differential with its surroundings increases. These two basic characteristics determine the overall temperature response of the tissue mass when a given energy pattern is applied.

In one exemplary embodiment, an energy probe and a temperature sensor are inserted into the organ or other tissue to be treated. The application of energy is controlled in a feedback loop to achieve the desired time-temperature curve. As a tissue mass is heated, a temperature gradient is created. When controlling for temperature, the approach is typically to attempt measurement at the center of heating, which is the hottest point, and to control for the temperature-time curve at that point. A control algorithm is applied so that the temperature rises at a controlled rate, and is then maintained at a peak (e.g., around 105° C. to ensure cell necrosis) for a set duration of time. This causes a lesion to develop at a controlled rate and to achieve a given ultimate size.

In deriving the appropriate temperature-time curve, tests are performed to determine what type/shape/size of "heat plume" is created within the tissue when temperature at the control point is brought to a target temperature at a particular rate and held in place for a specified period of time. Alternatively, sinusoidal or other varying signal patterns may be used. Tests for establishing the baseline curves would preferably be carried out on cadaver animals, however, computer simulations can also be used. Parameters that affect the time-temperature response to energy application will include size and type of animal, and may also include age. Once the temperature-time curves are determined, the next step is to determine the characteristics of the subject animal and match them to the parameters corresponding to a particular curve, then apply the energy according to the selected temperature-time curve.

In an alternative procedure, the appropriate temperature-time curve can be individually determined, or confirmed, for each subject animal by conducting a test sequence with the device. After the probe is inserted into (or placed against) the tissue, and prior to the main heating cycle, the device can be activated to apply a short series of fixed "pilot" power levels (joules/sec) while measuring the rate of temperature change (and its derivatives) associated with each level. The collected data can then be used to estimate the thermal mass and energy loss rate associated with the specific tissue mass that is being targeted. Using this information, the device would select from a appropriate range of temperature-time curves to be applied.

In one embodiment, the calculations can be made as the main device heating is in progress, without "pilot" heating rates, adjusting "on the fly" before the top temperature is reached.

As an alternative to the temperature-time curves, a set of power-time curves can be developed based upon the characteristics of the heat plume created under different conditions during initial tests. Using this approach, measurement of temperature during the actual procedure would not be required since the power can readily be monitored, and controlled, by the device. In embodiments where the tissue response is extremely well known for a particular application, and if it does not vary much across the patient population, a control algorithm which simply applies power in a given pattern over a given time can work sufficiently well without any feedback control based on measurements. Proper placement of the electrodes in the anatomy can be achieved through the use of one or more imaging techniques commonly used in the medical profession.

For applications where the target organ/tissue varies widely in size, mass and/or thermal properties across the population, the establishment of multiple temperature-time or power-time curves makes it possible to treat the full range of characteristics within that population using a single device, with automatic operation. The curves could consist of a finite set, or could be infinitely variable.

In one embodiment, the energy is controlled by using a temperature sensor that can either be mounted on or incorporated into the probe or separately inserted into the tissue to the desired treatment spot. The reading from this temperature sensor is then used to drive a feedback control loop to control the rate of application of the radio-frequency energy. A control algorithm is applied so that the temperature rises at a controlled rate, and then is maintained at a peak (e.g., 105° Celsius to insure cell necrosis) for a set duration of time. This causes a lesion to build at a controlled rate and to achieve a given ultimate size.

In another embodiment, the energy can be controlled by measuring the inductive resistance being exhibited in the tissue circuit, since this tissue property varies with temperature. A similar power control algorithm can be applied to this measurement to control lesion size.

In other embodiments, alternative energy sources can be used. Such energy sources include microwave, ultrasound, thermal, and any other energy type that can be focused at a target point within tissue to produce heat in a controlled manner. Regardless of the method of energy application, the rate, pattern and duration of energy application is controlled so that the lesion dimensions are controlled. In this manner, only the desired tissue area to be treated will be affected.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which:

FIG. 1 is an isometric view of a device for performing less invasive surgical procedures on animals according to one embodiment of the present invention;

FIG. 2 is a cross-sectional view of a device for performing less invasive surgical procedures on animals according to one embodiment of the present invention;

DETAILED DESCRIPTION OF THE INVENTION

Figure 3:
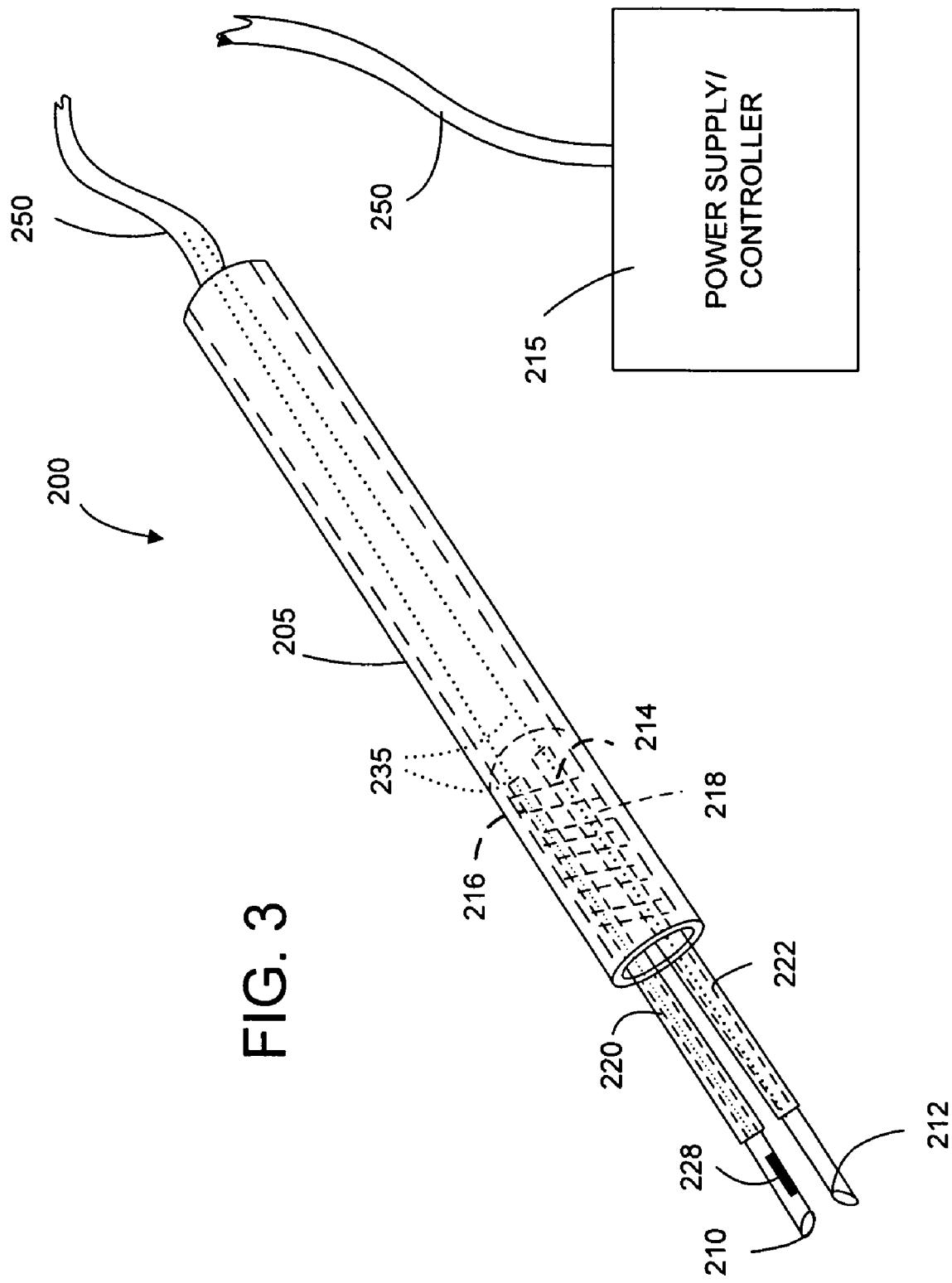
FIG. 3 is a diagrammatic perspective view of a second embodiment of the device for bi-polar applications.

Certain embodiments as disclosed herein provide for performing less invasive surgical procedures on animals. For example, one method as disclosed herein allows for electromagnetic energy to be applied in a controlled application and projected into the living tissue of the animal. The controlled application of the electromagnetic energy causes controlled heating of the living tissue beneath the surface. The heating of the living tissue beneath the surface causes cell necrosis, which modifies the living tissues without a surgical incision.

After reading this description it will become apparent to one skilled in the art how to implement the invention in various alternative embodiments and alternative applications, including those described at the end of this detailed description. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

One example of an application device for performing less invasive surgical procedures on animals according to one embodiment of the present invention is shown in FIG. 1, which is similar to the device disclosed in U.S. Pat. No. 6,911,027, which is incorporated herein by reference. The device 100 comprises a handle or housing 105 that has exterior dimensions that fit easily into a user's hand and has proximal and distal ends. A needle 110 formed of a conductive material and having proximal and distal ends is provided. The proximal end of the needle 110 can be mounted on the distal end of the housing 105 so that it is insulated from the housing 105.

The electromagnetic energy is conducted through the housing 105 to the needle 110. The housing 105 is adapted to be coupled to a power supply and controller 115 for supplying electromagnetic energy to the needle 110. In one embodiment, the power supply and controller 115 supplies radio frequency energy to the needle 110. The housing 105 is adapted to be coupled to the power supply and controller 115 for sensing the application of electromagnetic energy to the tissue and for controlling the application of the energy to the needle 110.

The housing 105 is configured to be readily grasped by the human hand. The housing 105 is formed of a suitable insulating material such as a plastic, rubber or polymer, which is molded into a desired shape that facilitates gripping and manipulation. Alternatively, the housing 105 can be formed of metal with appropriate insulating covering to prevent conduction to the user's hand. Generally, the material of which the housing is made should be tolerant of sterilization procedures such as surface washing and disinfecting. The device will likely be sold pre-sterilized in sealed packages using ethylene oxide (ETO) gas for sterilization, so the housing material should also be selected to withstand this treatment. Alternatively, or in combination, the devices may be radiation sterilized.

In the illustrated example shown in FIG. 1, the housing is substantially cylindrical, however, other shapes and exterior features, e.g., annular grooves, knurling, etc., may be used to enhance the ability to grip and manipulate the device. In the exemplary embodiment, the housing 105 has an outer surface 120 with a semi-hemispherical portion 121a at the proximal end, a cylindrical portion 121b extending from the proximal end, a tapered or conical portion 121c, and a smaller diameter cylindrical tip 121d.

A cross-sectional view of the device of FIG. 1 is shown in FIG. 2. The needle 110 is formed of a suitable conductive material, such as stainless steel or nickel-titanium alloy, which is capable of delivering the electromagnetic energy to the target area. The needle is mounted in the housing 105 so that it is stable and rigidly supported. As shown in FIGS. 1 and 2, the needle can be mounted on the distal end by directly molding it into the housing 105. The proximal end of the needle 110 is mounted in a carrier formed of a suitable material such as plastic or polymer, which is retained within the interior of housing 105.

A conductive assembly 135 extends through the housing 105 where it is connected at one end to the needle 110 and at the other end to a connection coupled to the power supply and controller 115 for supplying energy to the needle 110. Typically, this conductive assembly 135 includes a printed circuit board with appropriate contacts and terminates as a single conductor 140 which is electrically coupled to the needle 110 by suitable means such as solder. The conductive assembly 135 is connected at its proximal end to a flexible cable 142 secured to the proximal end of the housing 105. The flexible cable 142 carries a male adapter 145 (FIG. 1), which is adapted to be coupled via a female adapter (not shown) to a cable 150 (FIG. 1) to the power supply and controller 115 (FIG. 1). As will be readily apparent, the relative locations of the male and female connectors may be reversed.

In one embodiment, the device 100 is adapted to be coupled to the power supply and controller 115 for sensing the application of energy as it is supplied by the needle 110 to the tissue in the animal's body. Control for the application of radio frequency (or other) energy to the target tissue may be provided by one or more devices 155 for sensing temperature and/or impedance. Thus, the device 155 for sensing temperature and/or impedance can be mounted in the immediate vicinity of the portion of the needle 110 where it enters the housing 105, but preferably will be positioned closer to the tip of the needle so that the measurement of temperature/impedance is as close as possible to the location at which the energy is applied. The needle 110 is surrounded by an insulating cover over all surfaces except for the active area, typically the distal end of the needle, so that the energy is focused at the desired target area(s) and surrounding tissue is not affected.

An alternative embodiment of an application device 200 is provided in FIG. 3. Device 200 is adapted for bi-polar applications, where two needles 210 and 212 define a pair of electrodes separated by a gap or space which will be varied according to the desired shape of heat plume desired for a specified procedure. Each of the needles 210, 212 extends from a plug 218 formed from epoxy or other insulating material which holds the needles at a fixed spacing. The needles 210, 212 have a corresponding conductor 216, 214, respectively, at their proximal end which is connected within the insulating housing 205 to wires 235 or other electrical conductors to cable 250 which, in turn is connected to power supply/controller 215. Insulation 220, 220 covers needles 210, 212 so that only as much of the needles is exposed as needed to direct the energy to the desired point(s) within the tissue. The exposed tips will be fully inserted into the tissue, with the insulated areas also penetrating beneath the surface of the skin. This allows the energy to be released only at the center of the tissue to be treated, thus avoiding damage to the outer areas of the organ or tissue as well as skin or adjacent tissue through which the needles may have been inserted. The tips of the needles 210, 212 may be tubular, blade shaped, or formed with custom cross-sections to manipulate the electric field for a particular pattern. The wand-style applicator 200 is configured for gripping like a pencil, screwdriver or knife as desired by the user.

Temperature control is an important component in many procedures according to the present invention. Temperature feedback may be provided by a number of different mechanisms. As shown in FIG. 3, a temperature sensor 228 is incorporated in one of the needles (210) and connected via a conductor (not shown) which provides a signal to power supply/controller 215 to allow monitoring and power adjustment to reach a desired temperature ramp rate and target temperature for the procedure. A sensor 228 may be placed in both needles, which would allow the readings to be averaged for better accuracy.

Figure 4:
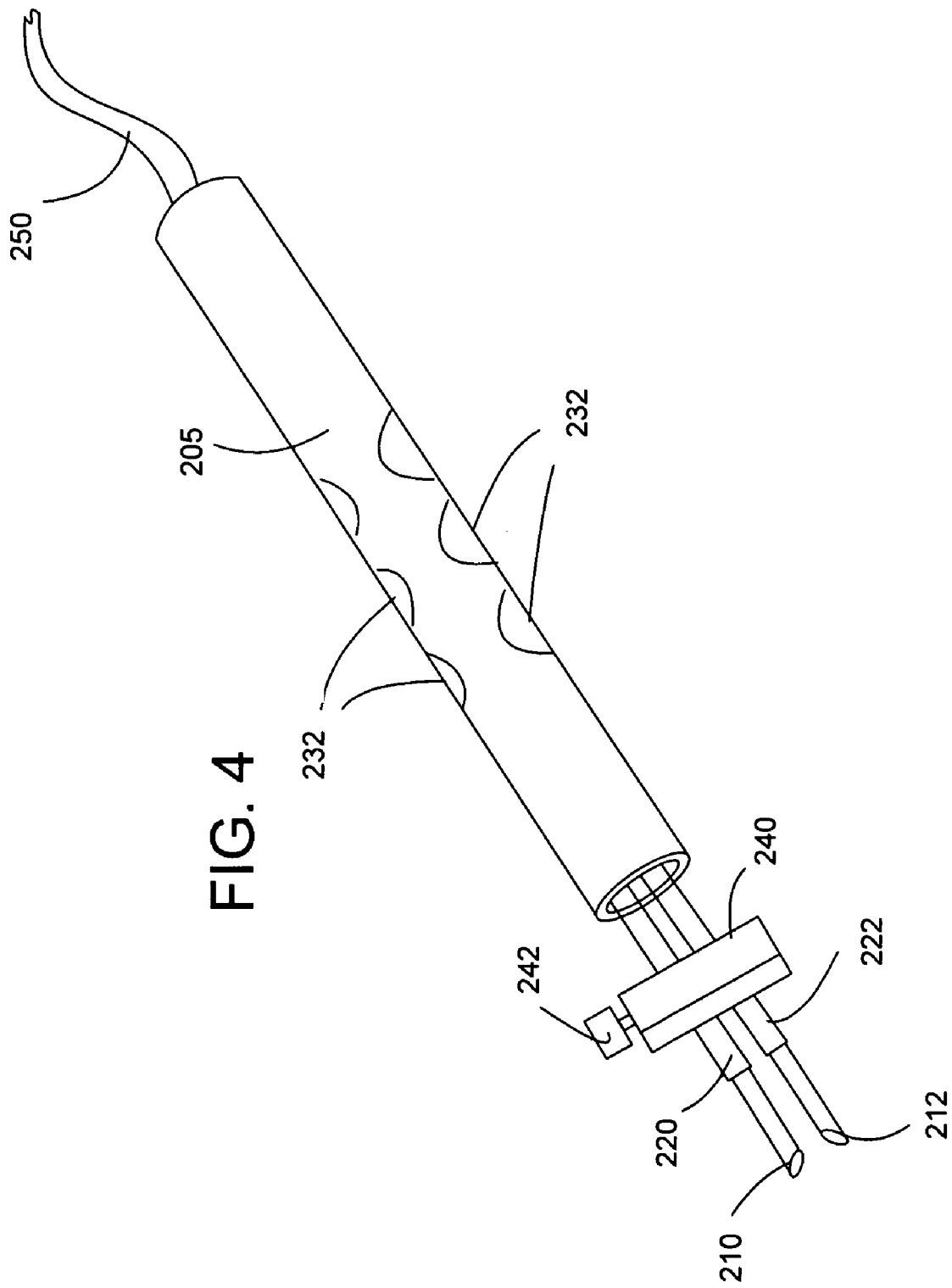
FIG. 4 is a diagrammatic perspective view of the second embodiment of the device with an adjustable stop for controlled positioning.

FIG. 4 illustrates an embodiment of the bi-polar device that includes a depth stop 240 that fits over the needles 210, 212 and is locked in place by a thumb screw 242 or similar releasable fastener. Depth stop 240 provides precise control over the depth to which the needle tips are inserted, preventing overshoot as well as providing a gauge for how deep the needles must be inserted to reach the desired target. Generally, the desired depth, and placement of the depth stop 240, will be determined via one or more of palpation of the area to be treated, look-up tables for animals of different sizes, e.g., miniature, small, medium, large and extra large which provide a preferred depth or depth range for an animal of a given size, or by appropriate medical imaging, such as ultrasound, X-ray, CAT scan, MRI or other known techniques. Depth markings may be imprinted or etched on the needles, so that the depth stop 240 need only be slid to the correct markings to prepare the applicator for use on a particular animal. Alternatively, depth markings can be used without depth stop 240 to provide a guide for depth of insertion. Also shown in FIG. 4 is a set of finger holds 232 formed in housing 205 to facilitate handling of the device.

Figure 5:
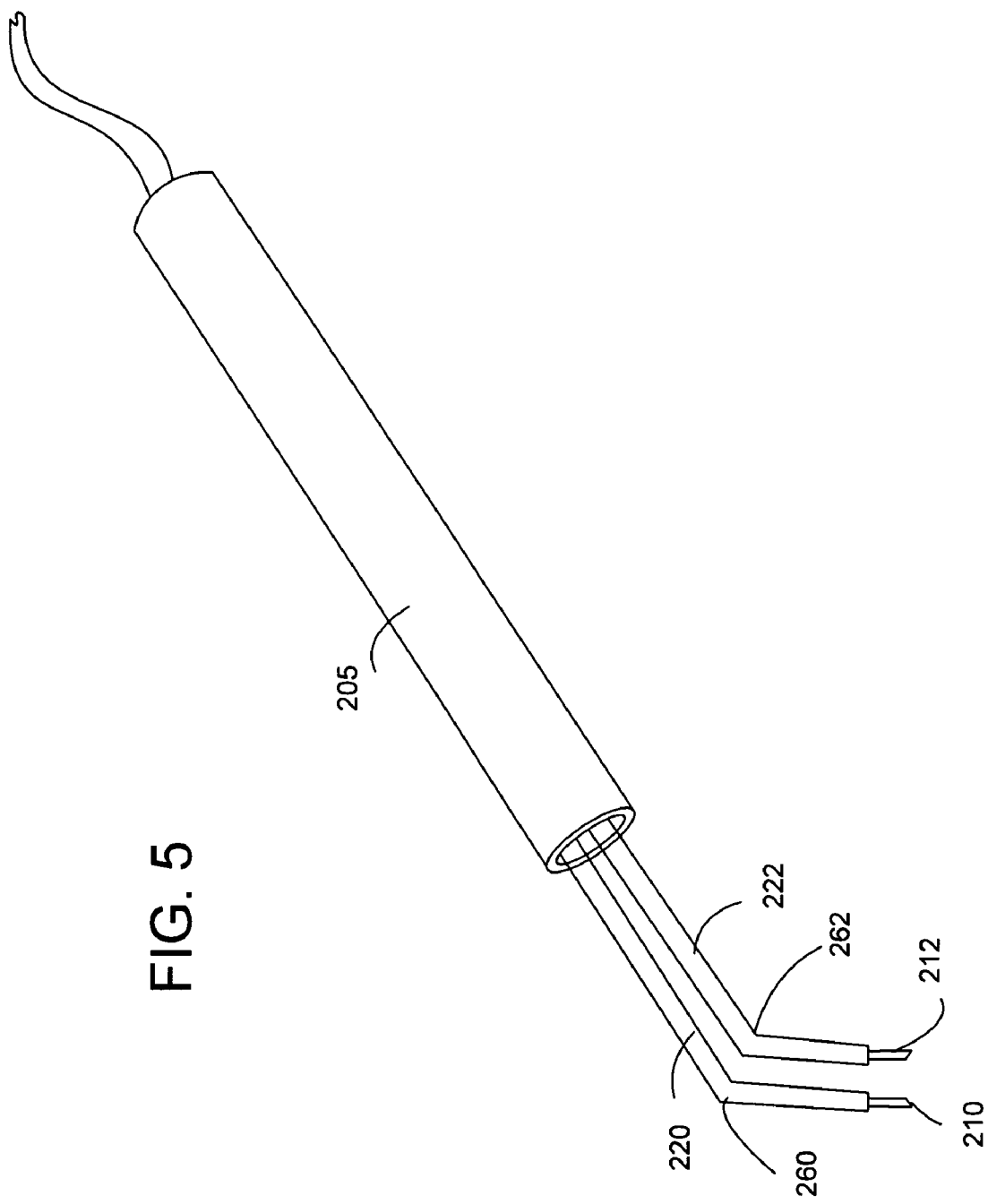
FIG. 5 is a diagrammatic perspective view of the second embodiment of the device with a modified needle configuration.

FIG. 5 illustrates an alternative embodiment of the bi-polar device in which the needles 210 and 212 extend at an angle defined by bends 260 and 262, respectively. As illustrated, insulation 220 and 222 extends to nearly the end of the needles, leaving only a small exposed area. Such a needle configuration is particularly useful for procedures requiring insertion through thicker sections of tissue that the user does not wish to be exposed to the treatment energy and/or for facilitating orientation of the insertion relative to the animal's anatomy, e.g., a dog's throat. Needle sets may be provided with curves instead of bends 260, 262, or with a variety of different angles for different anatomical structures and procedures.

The sizes of the applicators 200 will vary primarily in length of the exposed electrode surfaces, the spacing between the two needles, and the length of the insulated cover. It is anticipated that the lengths of the exposed electrodes as well as the spacing between them will fall within a range of about 0.8 mm (0.03 in) to about 25 mm (1.0 in.). The insulated portion can be varied widely to adjust the reach of the needles. The configuration of the housing 205 can also be varied according to the user's preference. For example, a pistol-style grip may also be provided.

Figure 6:
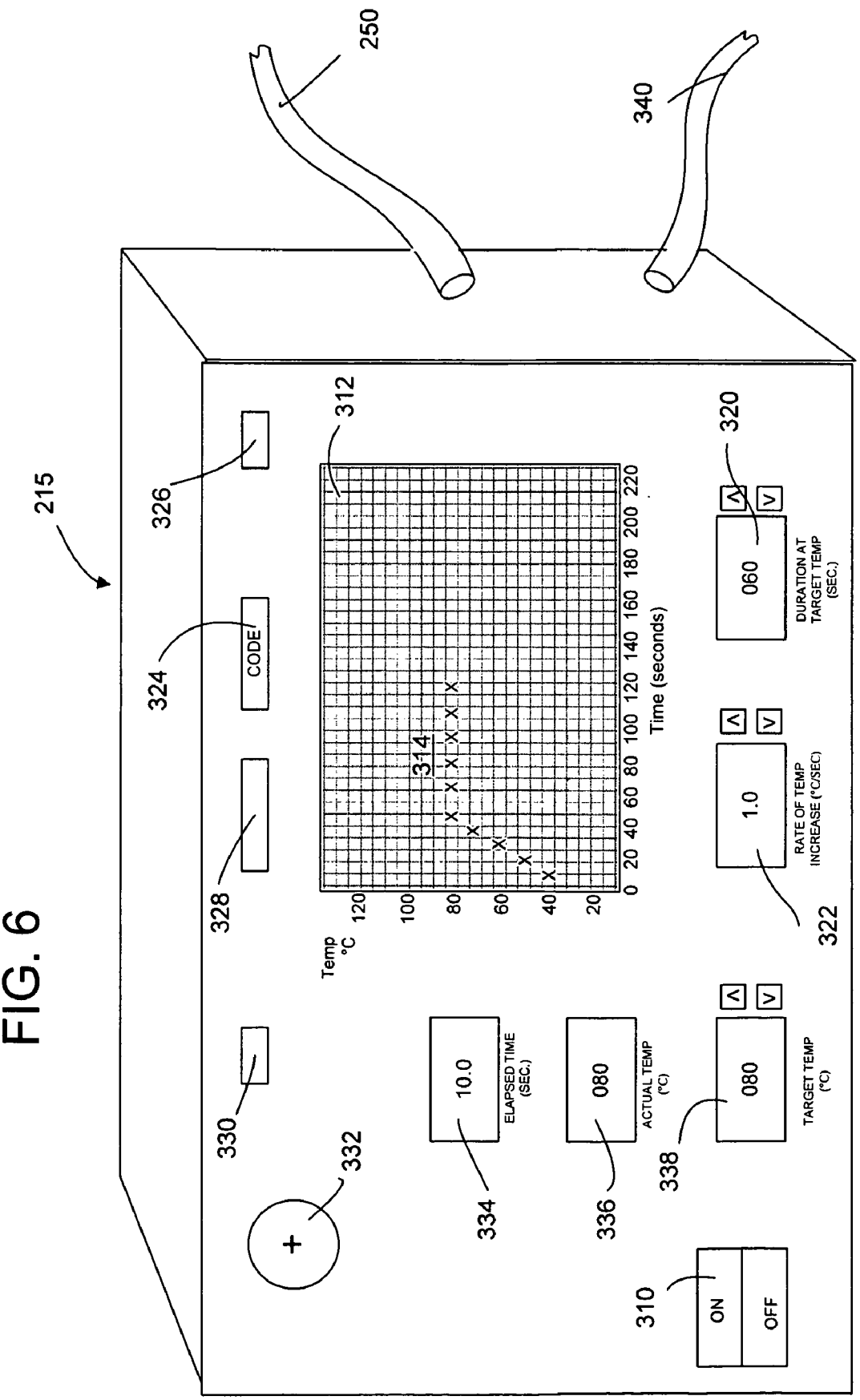
FIG. 6 is a diagrammatic view of an exemplary power supply/controller for use with the present invention.

FIG. 6 illustrates an exemplary general purpose temperature-controlled radio frequency power supply/controller 215 that provides the adjustability needed for virtually any procedure for less invasive surgery on an animal. The power supply/controller 215, also referred to as the "generator", is connected via power cord 340 to a standard voltage outlet (e.g., 110 VAC, 220 V/50 Hz) or other voltage source, to produce an RF energy output within the appropriate frequency range (around 460 kHz for inductive heating). The generator controls 320, 322 and 338 provide three user adjustable variables: 1) target temperature (degrees C.) via control 338, 2) rate of temperature rise as the temperature is brought up to the target (degree C. per second), via control 322 and 3) duration of time for which the target temperature is maintained after it is achieved (seconds), via control 320. Each of these parameters is discussed below:

Target Temperature: Depending on the desired result, one or more of three different effects will be selected, each dependant on temperature achieved. These are:

(1) Shrinkage alone (with as little cell necrosis as possible);

(2) Cell Necrosis with maximum creation of scar tissue; and (3) Cell Necrosis with as complete destruction of tissue as possible.

Shrinkage is achieved mainly due to collagen's propensity to shrink with heat. Collagen is present in connective tissue in places such as the vocal cords. Shrinkage of collagen and cell necrosis each proceed according to their own temperature-time relationship, however, there is some overlap between the two.

Collagen exposed to a temperature slightly above 60 degrees C. for several minutes will shrink significantly. If it is exposed to a temperature on the order of 75 degrees C., collagen will shrink by the same amount in just one second.

Cells exposed to a temperature of 50 degrees C. for about 50 seconds will die. Cells exposed to 105 to 110 degrees C. will die almost instantly because the liquid within the cells begins to boil at about this temperature.

Control 338 provides adjustability over a range of 45 to 115 degrees C. in one degree increments. As illustrated, control 338 includes a readout and up/down buttons for increasing and decreasing the desired temperature. It will be readily apparent that other types of controllers and readouts may be used and will remain within the scope of the invention. The time-temperature effect is discussed further below.

Rate of Temperature Rise: While a quick temperature rise can save time, it can have significant negative effects. If temperature is allowed to rise too fast, the immediate area around the electrodes can char, which blocks heat transfer and reduces the area of tissue ultimately heated. The more gradual the temperature rise, the more uniform the temperature in the heat plume.

Control 322 provides temperature ramping at rates in the range of 0.1 to 5.0 degrees C. per second. As illustrated, control 322 includes a readout and up/down buttons. Different types of controllers and displays may be used without deviating from the present invention.

Duration of Time at Target Temperature: When tissue is heated in the RF procedure, electric current heats the tissue in the area immediately surrounding the electrodes quickly while the surrounding tissue is heated more slowly by thermal conduction. This creates a heat plume with the target temperature near the electrodes and declining temperature progressing outward.

To achieve the objective of the procedure, target temperature must be set, and maintained long enough that the desired effect will be achieved over most of the heat plume volume.

The setting range for the Duration of Time at Target Temperature will likely be 0 to 999 seconds in one second increments, selectable by using the up or down adjustment of control 320. The numerical value of selected duration will be displayed on the display of control 320.

The user will be provided with recommended setting for these three variables for each type of procedure and situation. The recommended settings will be determined by animal studies and/or computer simulations. For example, in a vocal cord procedure (Example 2 below), if only seeking tissue shrinkage, the target temperature might be set for 70 degrees, with Duration at Target Temperature set fairly short, on the order of 30 seconds.

In the example of a neutering procedure (Example 1 below), to ensure that the tissue is dead while leaving a ball of scar tissue in place to simulate the testicle, target temperature might be set to 85 degrees C. and Duration at Target Temperature set longer, on the order of 120 seconds.

In the example of killing a tumor, where the goal would be to destroy the tumor completely if possible, a target temperature of 110 degrees might be set, but less Time at Target Temperature might be required, e.g., 90 seconds.

Generally, the slower the rate of temperature rise, the more uniform the temperature in the heat plume. Slow is better for results, but this must be balanced against time factors, such as the duration of anesthesia or a sedative. Tissue structures that are partially thermally isolated, such as a testicle or vocal chord, are easier to heat more uniformly than more massive, continuous tissue structures, so they likely will be able to be treated more quickly.

Graphical display 312 provides an output showing a real time plot 314 of temperature versus time. The display 312 will preferably be an LCD-type screen, but may also be an array of LEDs or other display means as are known in the art. The graph 314 may also be output to a peripheral device or a computer memory device to generate a record of the actual conditions during the procedure to be placed in the animal's treatment file.

The generator 215 has two switches, each with a corresponding indicator light. A system power switch 310 provides power to the unit and activates an LED indicator 326 to illuminate continuously when the power is on. An RF Power switch 332 feeds the RF power to the hand piece and causes an LED indicator 330 to be activated. Preferably, indicator 330 will blink when activated, and may be accompanied by an audible signal to ensure that the user is aware that energy is being applied.

A third LED indicator 328 will be activated if the RF power is interrupted as a result of detection of a safety shut off condition. A code number is displayed at display 324 to indicate the nature of the safety shut off condition. Examples of shut off conditions include, but are not limited to short circuits, power surges, over temperature, etc.

Generator 215 will be capable of generating higher wattages, perhaps 50 watts. However, the temperature control algorithm only calls for what wattage is needed to achieve the temperature, which is generally much smaller.

The following examples describe different procedures that may be performed using the above-described applicator and generator along with exemplary conditions for performing such procedures.

EXAMPLE 1

Less Invasive Neutering Procedure

Operation of the device 200 for use in the less invasive neutering of animals is now described as follows. The veterinarian estimates the size and relative positioning of the animal's testicles by palpation. He/she then selects from a range of probe sizes which would vary with respect to the exposed active length of the probe, for example, short, regular and long, to obtain a rough geometric fit to the testicle to locate the probe tip at its center, so that the heat plume will diffuse to produce the desired zone of cell death. Generally, the exposed active length of a uni-polar probe will be on the order of ½ the length of the testicle or longer. For bi-polar (two needle) probes, the spacing between the needles will be about ½ the length of the testicle.

For each probe size, the device has an associated a range of temperature control curves, from which the user (for manual control, using the evaluation described above) or device controller (with automatic control based on the thermal evaluation method described previously) would select the most appropriate based on the evaluation described above. For example, algorithms for each probe can be numbered 1 through 5, with each algorithm corresponding to a different time-temperature curve. A medium size, medium weight animal might call for a #2 algorithm from the group for a regular sized probe. By providing different probes and operating parameters, the full range of dog types and sizes could be covered.

Once the device 200 is connected to the power supply and controller 215, the veterinarian performing the procedure grasps the housing 205 of the device 200 by the fingers of a hand or in the palm of the hand and with the needles 210, 212 utilizes the housing 205 to cause the needles 210, 212 to penetrate the scrotum of the animal to a depth that will approximately center the active tip within the testicle. Alternatively, the needles 210, 212 can be inserted through the skin slightly forward of the scrotum, which is the typical incision site in current neutering procedures. When the appropriate probe (needle) size is selected, the insulation covering the proximal end of the needles 210, 212 protect against exposure of the skin and other tissue surrounding the testicle to the electromagnetic energy. Once correct positioning of the needles 210, 212 has been ascertained, the power supply and controller 215 can be activated to begin application of energy to the target tissue.

In an alternate embodiment, a uni-polar device 100 with a single needle 110 is utilized with a grounding pad being applied to the animal's skin to complete the circuit for application of the energy. The operation of the bi-polar and uni-polar embodiments is now described with reference to FIGS. 7 and 8, respectively.

Figure 7:
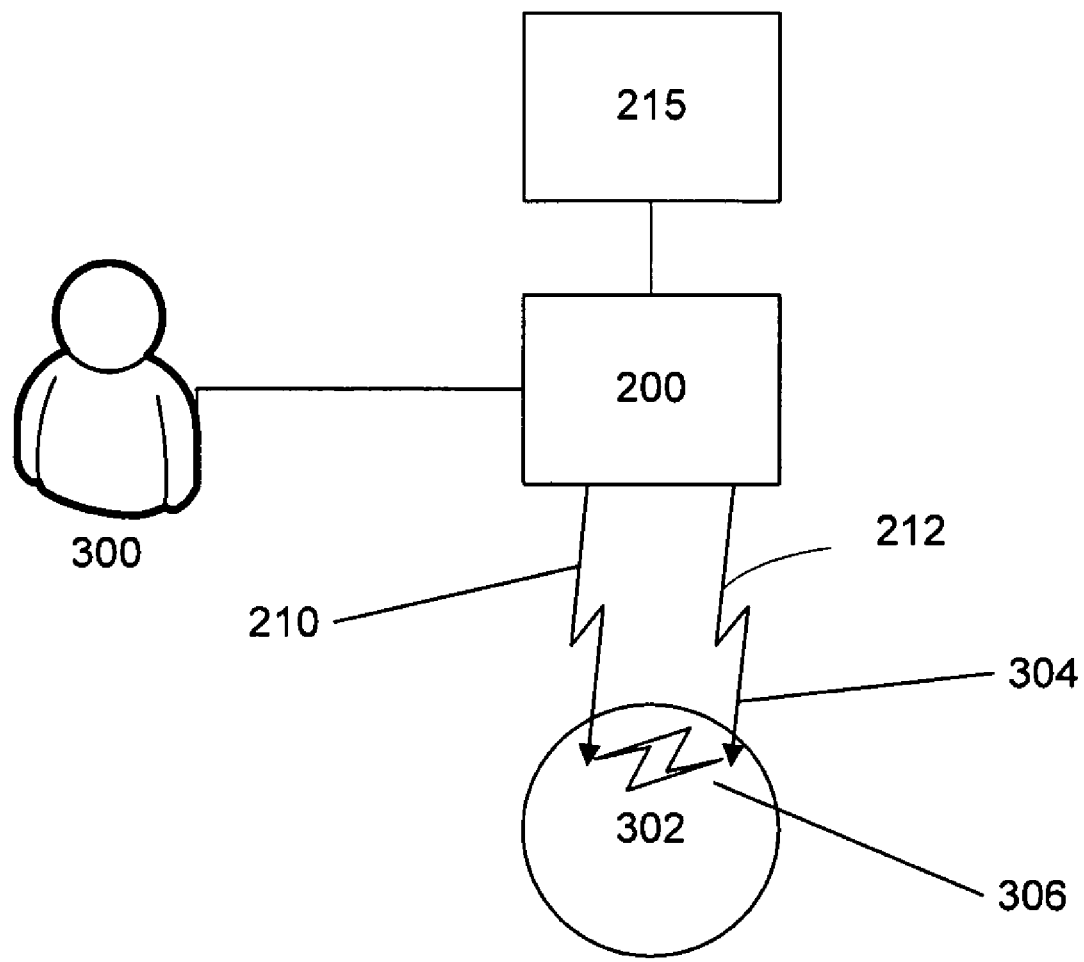
FIG. 7 is a block diagram of the device used in a bi-polar system according to an embodiment of the present invention.

FIG. 7 is a block diagram of the device 200 used in a bi-polar system 350 according to an embodiment of the present invention. The device 200 has an exposed, sharp-tip electrode with side walls that are electrically insulated proximate to the needles 210 and 212. The device 200 is connected to the power supply and controller 215.

After a user 300, such as a veterinarian, inserts the distal end of device 200 into the target tissue 302, the exposed electrode tip of needle 210 forms a closed electrical circuit 306 through the target tissue 302 to a second electrode 304 defined by the second needle 212. Proper placement of the electrode at or near the center of the target tissue 302, for this example, in the animal's testicle, can be achieved by palpation. The bi-polar system 350 can produce a lesion the shape of which can be controlled by the size, shape, and spacing of the electrodes as well as the rate of temperature climb and duration at peak temperature, or the power rate and duration of energy application, but may require multiple insertions to achieve the desired effect. For neutering, the procedure is repeated on the second testicle.

Figure 8:
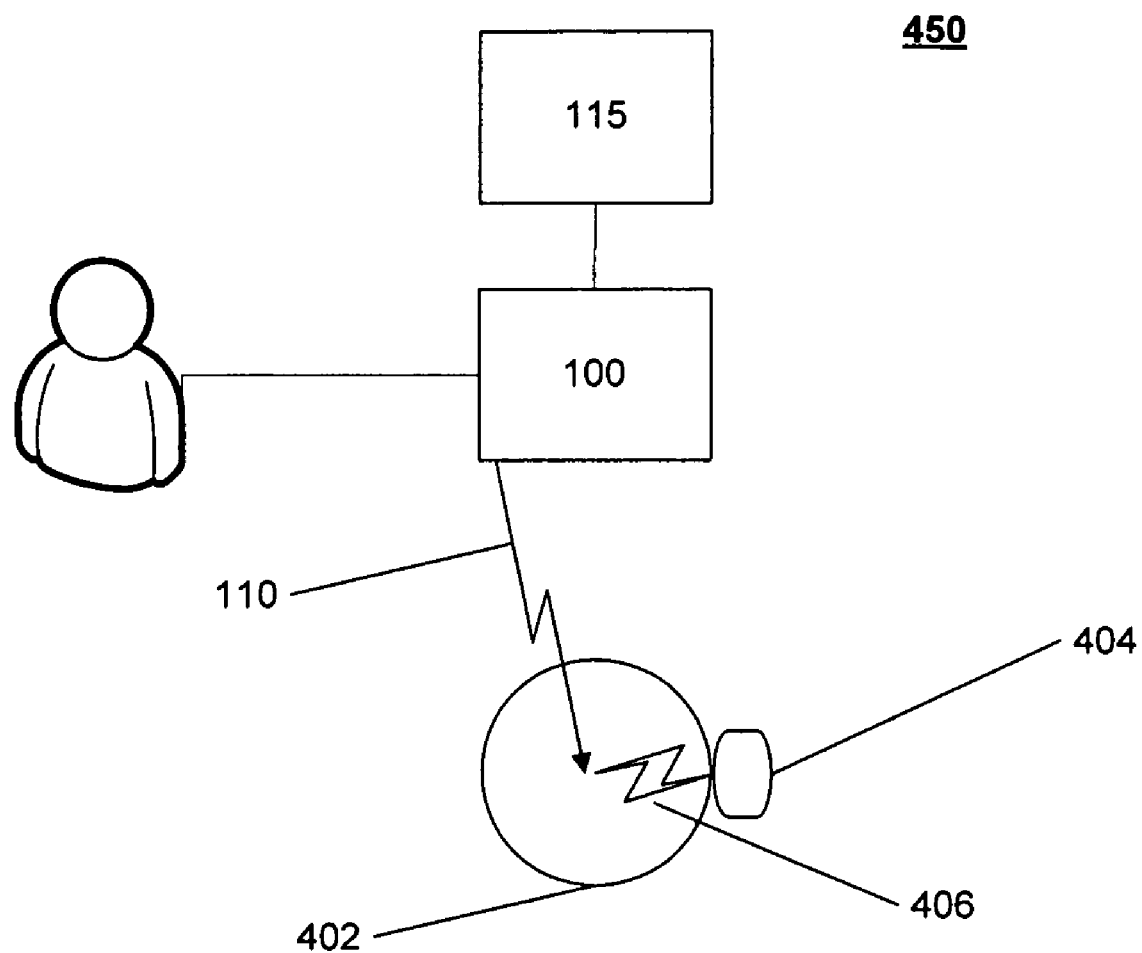
FIG. 8 is a block diagram of the device used in a uni-polar system according to an embodiment of the present invention.

FIG. 8 is a block diagram of the device 100 used in a uni-polar system 450 according to an embodiment of the present invention. As in FIG. 7, the device 100 is inserted so that the needle 110 enters the target tissue 402 (e.g., through the scrotum, once in each testicle). Multiple insertions of the device into the target tissue 402 may be necessary. Palpation can also be used for proper placement in the target tissue 402. The device 100 is connected to the power supply and controller 115 with the electrical circuit 406 closed through the animal's target tissue 402 by an electrode 404. In one embodiment, the electrode 404 is a broad, flat electrode that is taped or otherwise adhered, e.g., via conductive gel, to the animal's shaved skin (typically on the abdomen). The uni-polar embodiment of the device 100 generally produces a characteristic "jelly bean shaped" lesion. The size of the lesion can be controlled by a combination of the rate of temperature rise, peak temperature and duration, or by the power, rate and duration of energy application.

The electrode dimensions and control algorithms for either the uni-polar or bi-polar methods should be varied to suit the size and species of animal, based on the specific anatomy of the target tissue. It should be noted that other embodiments for the less invasive neutering of animals are also possible. For example, a surface probe can be used instead of the device 100 with the needle 110, or device 200 with needles 210, 212. The surface probe works by having both electrodes on a surface plate which is pressed against the outer tissue. The probe surface, which can be flat or curved to facilitate contact with the target area, can be cooled to protect the surface tissue while the energy radiates into the hidden tissue below the surface.

An alternative procedure for less invasive neutering can be performed by inserting the probe needle(s) into or close to the spermatic cord to collapse or block the tubes instead of ligating them.

It should also be noted that the power supply and controller 115, 215 has been described as providing electromagnetic energy in the form of radio waves. The advantage of RF over application of purely thermal energy, e.g., a heated needle, is that the RF energy excites the tissue volume between the electrodes to form a heat plume, while a heated needle radiates heat directly to the contacted tissue such that closest tissue may be burned by the time the surrounding tissue has been sufficiently heated to induce the desired degree of cell necrosis or shrinkage. The present invention, however, is not limited to the use of radio waves and generally is intended to cover the application of energy that can be focused either by mechanical, electromagnetic or electro-optical means to a desired point within the tissue to produce controlled heating. In one alternate embodiment, a microwave source (e.g., ~100 MHz and above) could be configured to focus energy to a target within the tissue without requiring physical insertion of probe, thus providing a non-invasive method of treatment. In other embodiments, other energy sources such as thermal heating or ultrasound may be used, although, as described above, thermal heating is less effective for formation of a heat plume. Regardless of the method of energy application, the rate, pattern and duration of energy application is controlled so that the lesion dimensions are controlled. In the case of neutering, the goal is to create a lesion large enough to render the testicle inoperable. After treatment, the testicle would shrink somewhat but stay in place as a mass of scar tissue.

The application of power can be controlled using Open Loop, Closed Loop or Adaptive Closed Loop methods.

Open Loop involves no measurement during the procedure, just the application of power in a controlled pattern and duration.

Closed Loop involves use of a temperature sensor and/or inductive resistance measurements to provide continuous feedback to control the application power such that temperature rises at a pre-set rate and is sustained ant a pre-set target temperature for a pre-set period of time.

The appropriate pre-set values are determined in prior studies of tissue response and/or by computer simulations of tissue response. The user must choose from the list of previously determined temperature patterns (as defined by the parameter settings they are given) based on characteristics of the patient, prior to starting the energy application.

Adaptive Closed Loop control has all the characteristics of Closed Loop Control, except that the device automatically chooses the appropriate temperature pattern based on tests it performs on the individual patient at the time of the procedure. These tests consist of the application of one or more "pilot" power applications and the observation of the temperature response of the tissue, by sensing the rate of temperature change and its derivatives, This allows the device to calculate a thermal mass and loss rate for the tissue involved and then to select a temperature pattern which will generate an appropriate heat plume. So the user does not need to select a temperature pattern.

Regardless of the type of control used, prior studies of tissue response, and/or computer simulations must be performed to determine how the heat plume is formed in the particular tissue structure when various levels/durations of power are applied.

Figure 9:
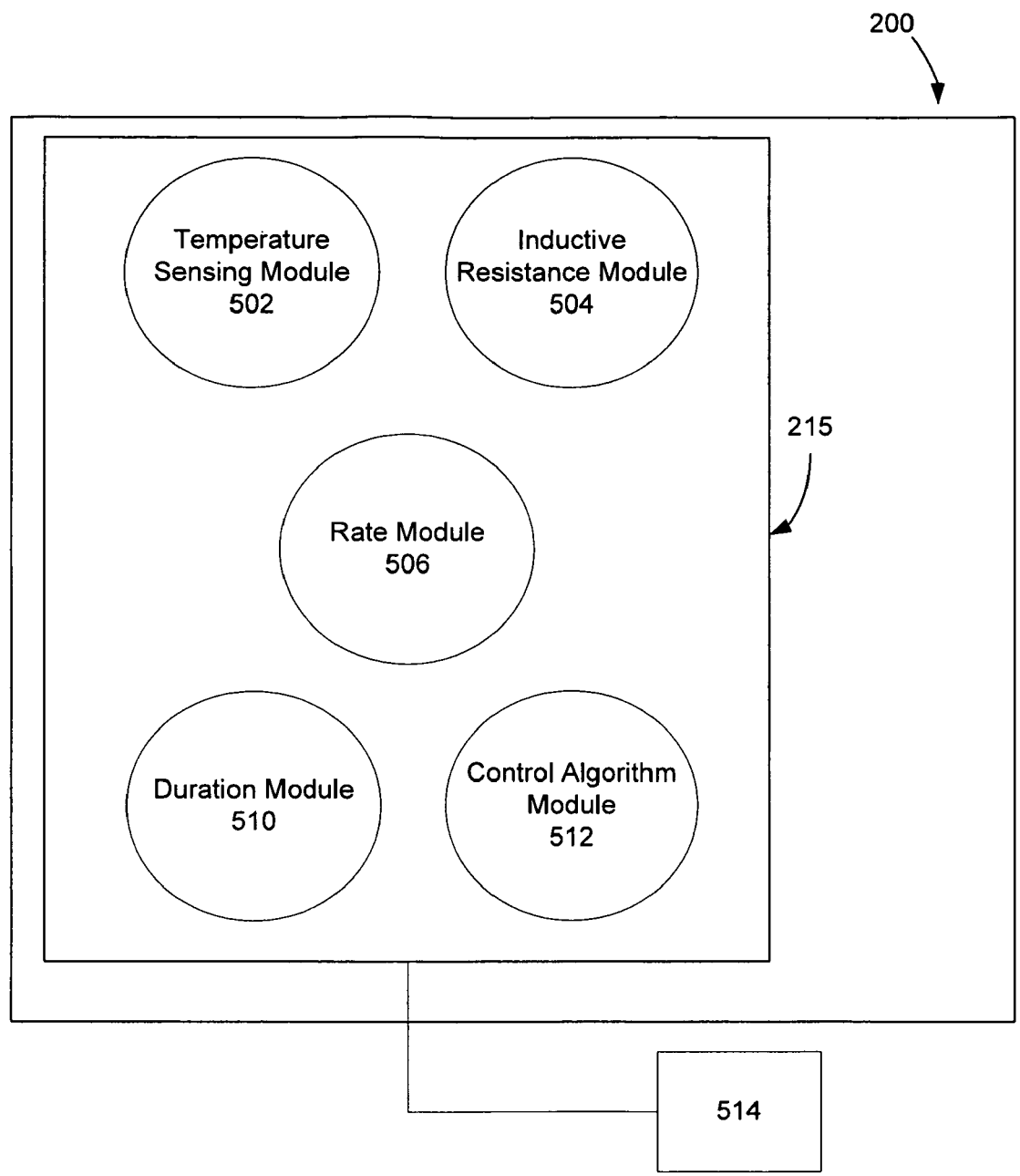
FIG. 9 is a block diagram of the device illustrating the control of the application of power according to an embodiment of the present invention.

FIG. 9 is a block diagram of the device illustrating closed loop control of the application of power according to an embodiment of the present invention. In FIG. 9, the device 200 includes the power supply and controller 215. The power supply and controller 215 includes a temperature sensing module 502, an inductive resistance module 504, a rate module 506, a duration module 510, and a control algorithm module 512. These modules can be controlled via a pre-set algorithm based on experimentally- and/or clinically-established parameters for specific procedures, or can be set manually by the user by way of controls 320, 322 and 338 of power supply/controller 215.

In the adaptive closed loop control method, the rate module 506 can determine the rate of electromagnetic energy to apply to the target tissue 514. The temperature sensing module 502, which is used for both closed loop and adaptive closed loop control, can be communicatively coupled to a temperature sensor that can be mounted on or incorporated in the device 200 or separately inserted into the target tissue 514 in some other manner.

The temperature sensing module 502 reads the temperature from the temperature sensor. The temperature sensing module 502 can use the reading from the temperature sensor to drive a feedback control loop to control the rate of application of the energy via the rate module 506. For example, a control algorithm in the control algorithm module 512 can cause the temperature to rise at a controlled rate as the rate module 506 controls the application of a given amount of energy. To that end, the temperature sensing module 502 can increase the temperature until the control algorithm module 512 determines that it has reached a desired peak. At that point, the control algorithm module 512 causes the temperature sensing module to maintain the peak temperature. In one embodiment, the peak temperature is 105 to 110 degrees C., which ensures cell necrosis. The temperature sensing module produces a readout that allows the user to read the ramp rate and when the target temperature has been achieved within the tissue.

The control algorithm module 512 will cause the temperature sensing module 502 to maintain the peak for a set duration of time. To that end, the duration module 510 can start a timer or other internal clock mechanism. When the duration module 510 determines the set duration has elapsed, the control algorithm module 512 can reduce or stop the application of energy to the target tissue 514. Alternatively, the user can manually set a timer for duration at temperature once the target temperature has been achieved. This allows a lesion to spread at a controlled rate and to achieve a given ultimate size in the target tissue 514.

In an embodiment using a closed loop method, both the needle and temperature sensor are inserted into the target tissue. The algorithm for application of energy uses a closed feedback loop control scheme to achieve the desired time-temperature curve. As a tissue mass is heated, a temperature gradient is created. When controlling for temperature, the approach is typically to attempt measurement at the center of heating, which is the hottest point, and to control for the temperature-time curve at this point. A control algorithm is applied so that the temperature rises at a controlled rate, and is then maintained at a peak (typically 105° C. to ensure cell necrosis) for a set duration of time.

In deriving the appropriate temperature-time curve, tests are performed to determine the type/shape/size of the "heat plume" that is created within the tissue when temperature at the control point is brought to a target temperature at a controlled rate and maintained for a specified period of time. These curves can saved in the form of a look-up table and/or stored within a device controller for selection by the user through entry of parameters such as target tissue type, animal size, and other relevant characteristics.

When using Adaptive Closed Loop control the desired temperature-time curve can be individually determined for each animal by a test sequence performed as part of the full procedure. After the probe is inserted into (or placed against) the tissue, and prior to the main heating cycle, the device is activated to apply a short series of fixed "pilot" power levels (joules/sec) and measure the rate of temperature change associated with each level. Using the collected data, the derivatives of the rates of temperature change are calculated and used to generate overall temperature response curves for determining thermal mass and inherent losses associated with the specific tissue mass that is being targeted. Using this information, the user or the device controller would select from a range of temperature-time curves to apply. This would allow the device to create an appropriately adjusted heat plume for a range of sizes and characteristics of the target organs across the patient population.

In one variation of an adaptive closed loop controller, the calculations can be made as the main device heating is in progress, without "pilot" heating rates, adjusting "on the fly" before the top temperature is reached.

In another embodiment, the energy can be controlled by measuring the inductive resistance produced within the tissue circuit, since the tissue resistance correlates directly with temperature. The inductive resistance module 504 can be communicatively coupled to a meter that can be incorporated in or mounted on the device 200. In this embodiment, no temperature sensor is required since the resistance measurement itself can be used to provide the indication of temperature. However, since the temperature/resistance correlation is not linear, resistance-time curves may need to be generated.

The inductive resistance module 504 reads the temperature or other inductive resistance related measurement as the rate module 506 applies energy. The inductive resistance module 504 uses the reading to drive a feedback control loop to control the rate of application of the energy. For example, a control algorithm in the control algorithm module 512 can cause the energy to be applied at a controlled rate.

To that end, the inductive resistance module 504 can increase the temperature until the control algorithm module 512 determines that the inductive resistance has reached a peak level. At that point, the control algorithm module 512 causes the inductive resistance module 504 to maintain the peak inductive resistance measurement for a set duration of time. To that end, the duration module 510 can start a timer or other internal clock mechanism. When the duration module 510 determines the set duration has elapsed, the control algorithm module 512 can reduce or stop the application of energy to the target tissue 514. This causes a lesion to build at a controlled rate and to achieve a given ultimate size in the target tissue 514.

In another embodiment, the control algorithm module 512 can apply a power control algorithm to control lesion size. In embodiments where the tissue response is extremely well known for a particular application, and if it does not vary much across the patient population, the control algorithm module 512 may apply power in a pre-determined pattern over a specified period of time in an open loop system, without any feedback control based on measurements.

An open loop control scheme may be used to achieve the same effect as the closed loop system described above, however, extensive additional testing would be required to determine an optimal energy application pattern which would yield an allowable range of temperature responses to in turn yield an allowable range of heat plume sizes. This added layer of variability requires more detailed knowledge of the thermal response of the treatment area. An exemplary method of open loop control for heating tissues is disclosed in U.S. Patent Publication US2007/0050001 of the present inventor, which is incorporated herein by reference.

Figure 10:
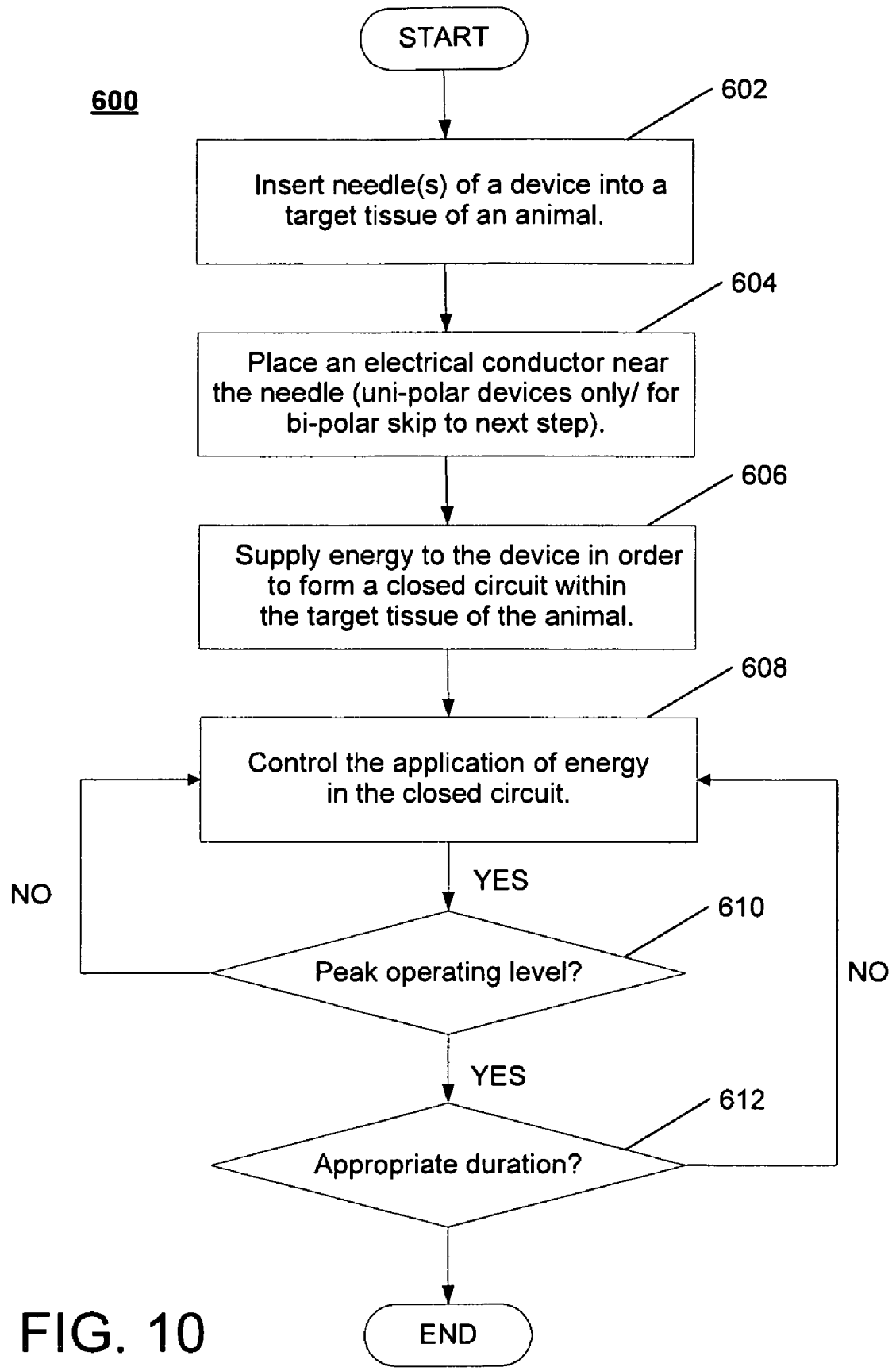
FIG. 10 is a flowchart of a method for performing less invasive surgical procedures on animals according to an embodiment of the present invention.

FIG. 10 is a flowchart of a method for the less invasive neutering of animals according to an embodiment of the present invention. The method 600 begins at step 602 where a veterinarian or other qualified individual inserts a needle of a device (such as one of the devices shown in FIGS. 1 through 5) into the target tissue of an animal. At step 604, a second electrical conductor is placed in a position that will allow a circuit to be completed between the second conductor and the needle. The second electrical conductor can be, for example, a second needle fixed at a pre-determined separation, on the order of a few millimeters up to about 2.5 centimeters (~1 inch), from the first needle, or a broad, flat electrode. If the broad, flat electrode in a uni-polar device is much larger than the needle, the distance between the two electrodes can be much greater. With bi-polar devices, such as those shown in FIGS. 3-5, the two needles will be inserted simultaneously such that step 604 will be skipped. In either case, a second electrical conductor is located within a sufficient distance from the first electrical conductor so that a closed circuit of energy can be created.

At step 606, energy is supplied to the device. The supplied energy creates the closed circuit of energy in the target (testicular) tissue of the animal. At step 608, the application of the energy to the closed circuit is controlled as follows. At step 610, it is determined whether the peak operating level is achieved in the target tissue. For example, a power control algorithm, in conjunction with one or more sensors, can determine if the temperature in the tissue has reached a desired level. In another embodiment, inductive resistance measured in the closed circuit can be used to indicate to the power control algorithm when the peak operating level has been achieved.

If step 610 is false, the process repeats, wherein the tissue continues to be heated until the peak operating level is reached. Thereafter, at step 612, the system determines if the appropriate duration has been achieved. For example, once peak operating temperature or peak operating inductive resistance occurs, the peak level should be maintained for a given period of time. Step 612 repeats until a timer indicates that the required duration has been reached. Thereafter, the tissue of the animal has been ablated in a more humane and less invasive manner and the method 600 is complete.

EXAMPLE 2

De-Barking or Reducing Barking Volume

Operation of the device 200 for use in the less invasive noise reduction in animals is now described as follows. Using conventional medical imaging techniques such as X-ray, laparoscopy or other method, the veterinarian estimates the size and relative positioning of the dog's vocal chords. He/she then selects from a range of probe sizes which would vary with respect to the exposed active length of the probe, for example, short, regular and long, to obtain a rough geometric fit to the throat and vocal chord to locate the probe tip at its center, so that the heat plume will diffuse to produce the desired zone of cell death and/or collagen shrinkage.

For each probe size, the device has an associated a range of temperature control curves, from which the user (for manual control) or device controller (with automatic control) would select the most appropriate based on the evaluation described above. For example, algorithms for each probe can be numbered 1 through 5, with each algorithm corresponding to a different time-temperature curve. A medium size, medium weight animal might call for a #2 algorithm from the group for a regular sized probe. By providing different probes and operating parameters, the full range of dog types and sizes could be covered.

Once the device 200 is connected to the power supply and controller 215, the veterinarian performing the procedure grasps the housing 205 of the device 200 by the fingers of a hand or in the palm of the hand and with the needles 210,212 utilizes the housing 205 to cause the needles 210, 212 to penetrate the neck area of the animal in order to contact the vocal cord tissue in each of the vocal cords. When the appropriate probe (needle) size is selected, the insulation covering the proximal end of the needles 210, 212 should protect against exposure of the skin and other tissue surrounding the vocal chords to the electromagnetic energy used for heating. After the proper positioning is attained, which may be confirmed by X-ray or other imaging technique, the power supply and controller 215 can be turned on.

The inventive device and method can also be used in a procedure that accesses the vocal chords through the mouth and down the throat while the animal is fully sedated or under general anesthesia. Advantages are provided through the controlled application of focused energy, which generally produces predictably limited scarring as opposed to healing of an incision, which can vary widely among individual animals. In addition, the lower temperature settings can be used to shrink collagen rather than inducing cell necrosis.

Referring again to FIG. 3, the device 200 is inserted so that the needles 210, 212 enter the target tissue 402 (e.g., through the neck, one or more times in each vocal cord). Multiple insertions of the device into the target tissue 402 may be necessary. Palpation can also be used for proper placement in the target tissue 402. The device 200 is connected to the power supply and controller 215 with the electrical circuit 406 closed through the animal's target tissue 402 by an electrode 404.

If the desired procedure involves completely disabling the vocal cords, a higher temperature or longer duration may be used. However, in a preferred embodiment, the goal will be to reduce the volume of the bark, which can be achieved by collagen shrinkage. For such a procedure, a temperature in the range of 60 to 65 degrees C., preferably about 62 degrees C., could be used with an exposure in a range of around 30 seconds to 5, or as many as 10, minutes. Alternatively, a temperature of 75 degrees can achieve the same effect in about 1 second.

EXAMPLE 3

Sterilization of Female Dogs

Using the device and general methods described above, sterilization of a female animal can be achieved by insertion of needles 200, 210 from outside the body or through the vaginal opening. Either the ovaries would be destroyed in a similar fashion to the testicles, as described in Example 1, or the fallopian tubes can be collapsed or blocked with scar tissue; possibly both steps at the same time. The organs would be physically shrunken in the process.

EXAMPLE 4

Correction of "Slipping Kneecaps" in Small Dogs

Small dog breed frequently exhibit a detrimental condition commonly referred to as "Slipping Kneecaps". This results in the dog frequently stumbling and experiencing pain in the joint. Severe cases are currently treated with surgery.

This condition occurs because the patella ligament, which runs vertically in a shallow depression (trough) in the kneecap and holds the knee joint together, elongates slightly and pops out of the depression. The patella ligament is held centered in the depression by two collateral ligaments, one on either side. For the patella ligament to pop out of position would require the patella ligament to elongate and most likely for at least one of the collateral ligaments to elongate.

These ligaments are connective tissue containing collagen, so they can be shrunk by RF heating, thus decreasing their length and putting them under greater tension, thus correcting the condition.

The patella ligament can be palpated back into position. The RF probe can then be inserted through the skin and into the patella ligament. RF energy can then be applied with temperature control to achieve a temperature of approximately 65° to 85° C. This will shrink a portion of the collagen tissue and slightly shorten the ligament, increasing its propensity to stay in the trough. Either the uni-polar (100) or bipolar (200) applicator embodiments may be used for this procedure.

Optionally, the collateral ligament which would likely have had to elongate to let the patella ligament move out of position, could also be shortened in a similar way to further stabilize the patella ligament in its correct position.

EXAMPLE 5

Treatment of Braceocephallic Syndrome in Small "Flat Faced" Dog Breeds

The small flat faced breeds of dog (such as pugs) commonly experience this syndrome which interferes with their breathing. The condition involves a set of mutually reinforcing detrimental features which include an elongated soft pallet, constricted nasal passages and laryngeal sacules. The elongated soft pallet tends to collapse into and block the air passage. The other features restrict the size of the air passage due to excess tissues.

This condition causes the dog to fatigue easily and to gag and snore, and makes them particularly sensitive to temperature fluctuations. In fact, many airlines have refused to transport flat faced dogs because of their vulnerability to the elevated temperatures that may be encountered during air travel, particularly during summer months.

A needle style RF probe with temperature control (uni- or bi-polar) could be inserted though the mouth and into the soft pallet. Application of RF energy would be applied to do the combination of shrinking the tissue, removing volume by ablation and stiffening through scar formation (or any advantageous combination of one or more of the three).

This modification of the tissue structure would reduce the propensity of the pallet to collapse into the airway.

A needle style RF probe (uni- or bi-polar) could be inserted through the nostrils and into the lining of the nasal passages. These lining tissues can be shrunken and ablated to increase the effective size of the air passages. This would also help the condition. The laryngeal sacules can also be shrunken and ablated by probing through the mouth.

EXAMPLE 6

Treatment of Collapsing Trachea

This condition is another ailment common in certain types of dogs, particularly toy breeds including pomeranians, chihuahuas and poodles, which restricts breathing and can choke the animal. It can also occur in miniature horses. In this condition, the trachea losses rigidity and collapses, closing the air passage. Dogs suffering from this condition are often required to live restricted lives with limited exercise. For treatment, a needle style RF probe (uni- or bi-polar) can be inserted through the neck or through the mouth and into the wall of the trachea. Tissue shrinkage, e.g., collagen shrinkage, can reduce excess tissue and controlled scarring can improve stiffness. Thus, the tendency of the trachea structure to collapse can be reduced.

EXAMPLE 7

Treatment of Laryngeal Paralysis

Laryngeal paralysis occurs in large dogs and horses, mainly as they age and can cause restriction of the breathing passage. The larynx has a pair of cartilage flaps called the laryngeal cartilages which are opened by muscles to clear the passage for breathing. In the condition, the nerves that control these muscles fail so the cartilages do not pull aside, out of the air passage. This leads to inadequate ventilation during exercise and during thermoregulatory panting as well as incomplete protection of the airway during swallowing. Affected animals thus have reduced tolerance for exercise and heat and an increased risk of aspiration pneumonia. This condition occurs in large dogs and horses.

The current treatment for laryngeal paralysis is a major surgical procedure which involves going in through the neck and suturing back the arytenoid cartilage permanently in an open position. This has the negative side effect of increasing the chance of the animal getting pneumonia. Also, because the tie-back procedure prevents the animal from sealing the larynx, it will no longer be able to swim or play in deeper water because drowning could occur. For water-loving dogs, this could represent a significant loss of regular favorite activities.

The proposed alternative using the inventive procedure would be to insert an RF needle probe (uni- or bi-polar) through the mouth and into either one of the cartilages or the connective tissue between the cartilage and the controlling muscles. Tissue would be ablated to create a smaller air passage than is done in the surgical procedure. Aside from bring less invasive, this would have the advantage of reducing the likelihood of the dog drowning.

EXAMPLE 8

Reduction/Removal of Fatty Tumors

A common condition that can occur in dogs, and is especially common in the retriever breeds, is the development of benign fatty tumors just under the dog's skin. These tumors can be prone to irritation and infection, and can sometimes become so large as to be unsightly and/or present an impediment to the dog's movement. When the tumors become too large or cause friction with other body parts they are sometimes surgically removed. Smaller growths are often left in place to avoid surgery.

A needle style RF probe could be inserted through the skin into the tumor. RF induced heat would ablate (higher temperature) or shrink (lower temperature) the tissue. If excess fat were to remain, it would be liquefied by the heat and could be drawn out by a vacuum passage in the probe or by a separate syringe.

EXAMPLE 9

Treatment of Chronic Heel Pain Syndrome in Horses

Yet another procedure that can be performed using the inventive device and method is treatment of horses that have developed chronic pain in the back of their heels due to structural deterioration from repetitive stress. This condition, frequently known as "navicular disease", can significantly diminish the horse's quality of life, with intermittent to continuous lameness and medication for the remainder of the horse's life. When other treatments fail, apart from euthanasia to avoid a life of pain for the animal, CHPS can be treated by surgical posterior digital neurectomy, or "nerving".

An RF needle probe can be used to perform the procedure less invasively and more quickly, which is particularly advantageous since a common practice is to perform the procedure under a local anesthetic, while the horse is standing. Alternatively, it could be used to treat the actual condition by stiffening connective tissues.

EXAMPLE 10

Ligament and Tendon Repair in Horses

Another procedure that is performed on horses is repair of suspensory ligaments and flexor tendons. Fracture of these connective structures in the legs of a horse can be so serious as to sometimes require euthanasia. While healing, the fracture site tends to attach itself to surrounding tissue to which it should not be connected. This has the effect of preventing the ligament and tendons from fulfilling their mechanical function.

An RF needle probe could be inserted into the misconnected area and, using tissue ablation, the ligament or tendon can be released from the improperly connected tissue so it can move more correctly.

It also may be possible to use the RF probe to trim unevenness where separated parts of the tendon are healing, to allow the tendon to move correctly. In addition the present invention may be used to help fuse loose ligament and tendon ends together through collagen shrinkage.

EXAMPLE 11

Hyperthyroidism in Dogs

Hyperthyroidism occurs when too much thyroid hormone is created and released from the thyroid gland. The reason that the gland secretes more hormones is because the gland enlarges and becomes overactive. Generally, the enlargement is due to a benign growth. Although not cancer, the overactive thyroid can cause life-threatening problems. On the other hand, surgical removal of the thyroid requires that the dog take thyroid medication for the remainder of its life.

Using the device and method of the present invention, hyperthyroidism can be treated without surgical removal by using RF ablation to reduce the size of the thyroid gland. The thyroid gland lies on the dog's trachea, just below the larynx. The probe needle(s) are inserted through the animal's neck below the larynx. In most cases, the goal is tissue shrinkage rather than destruction, so a lower temperature and/or lower time may be used to limit the ablation to remove/destroy a small volume of the gland. In some cases, however, completely disabling the thyroid gland may be required, so higher temperature and/or longer time combinations would be appropriate.

Those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

The invention claimed is:

1. A method for performing a surgical procedure on an animal, comprising:
    determining a size and thermal mass of a target tissue to be treated;
    inserting a needle having an insulating body, a proximal end, and a first electrode at a distal end into the target tissue so that the electrode is substantially centered within the target tissue, wherein the proximal end of the needle is in electrical communication with a power supply and a controller;
    positioning a second electrode at a distance from the needle to create a circuit across the target tissue; and
    applying focused energy within the target tissue at two or more of a pre-determined power level, a pre-determined temperature ramp rate, a pre-determined temperature and a pre-determined period of time based on the thermal mass and thermal losses of the target tissue to form a heat plume within the target tissue to induce one or more of cell necrosis, collagen shrinkage and scar formation without damage to tissue surrounding the target tissue.

2. The method of claim 1, wherein the needle has a temperature sensor disposed therein.

3. The method of claim 2, wherein the step of applying focused energy comprises activating a power supply and a controller for applying energy to the needle to form the heat plume within the target tissue.

4. The method of claim 3, further comprising measuring a temperature within the target tissue, and selecting within the controller a time-temperature curve corresponding to tissue response of the target tissue.

5. The method of claim 3, wherein the controller includes a control algorithm module configured to implement a feedback loop, the feedback loop adapted to continually receive a signal from the temperature sensor and cause the controller to control the energy applied to the needle to increase the sensed temperature until a peak operating level is obtained in the target tissue of the animal.

6. The method of claim 3, wherein the controller includes a control algorithm module configured to implement a feedback loop, the feedback loop adapted to continually sense a resistance level and cause the controller to increase the resistance level until a peak operating level is obtained in the target tissue of the animal.

7. The method of claim 3, further comprising, after inserting the needle into the target tissue, and prior to the step of activating the power supply and controller, performing a test comprising:
    activating the power supply and control to apply a short series of pilot power levels;
    measuring a rate of temperature change associated with each pilot power level; and
    collecting the measured rate of temperature change associated with each pilot power level to estimate the thermal mass and energy loss rate associated with the target tissue.

8. The method of claim 7, wherein the step of collecting further comprises calculating derivatives of the measured rate of temperature change to generate time-temperature curves.

9. The method of claim 1, wherein the energy is radio frequency energy.

10. The method of claim 1, wherein the second electrode comprises a second needle disposed at a fixed separation from the needle, wherein the fixed separation is selected based upon a desired volume of the heat plume to be generated within the target tissue.

11. The method of claim 1, wherein cell necrosis is induced and the pre-determined temperature is within a range of about 50 to 110 degrees Celsius.

12. The method of claim 1, wherein collagen shrinkage is induced and the pre-determined temperature is within a range of about 60 to 75 degrees Celsius.

13. The method of claim 1, wherein the pre-determined ramp rate is in the range of about 0.1 to 8.0 degrees C. per second.

14. A method for performing a surgical procedure comprising neutering a male animal, the method comprising:
- palpating one of the animal's testicles to determine the size;
- determining a thermal mass of the animal's testicle;
- selecting a needle having a needle length, based upon the size of the animal's testicle, the needle further comprising an insulating body, a proximal end, and a first electrode at a distal end,
- inserting the needle into the animal's testicle so that the first electrode is substantially centered within the animal's testicle, wherein the proximal end of the needle is in electrical communication with a power supply and a controller;
- positioning a second electrode at a distance from the needle to create a circuit across the animal's testicle; and
- applying focused energy within the animal's testicle at two or more of a pre-determined power level a re-determined temperature ramp rate a pre-determined temperature and a pre-determined period of time based on the thermal mass and thermal losses of the animal's testicle to form a heat plume within the animal's testicle to induce cell necrosis without damage to tissue surrounding the animal's testicle.

15. The method of claim 14, further comprising repeating the procedure for the other testicle.

16. The method of claim 14, wherein the pre-determined temperature is in the range of 85 to 105 degrees C. and the pre-determined period of time is about 120 seconds or more.

17. A method, for performing a surgical procedure comprising bark reduction in a dog, the method comprising:
- determining a thermal mass of the dog's vocal cords;
- inserting a probe having an insulating body, a proximal end, and a distal end having a first electrode and a second electrode into the dog's neck so that the first and second electrodes are within the dog's vocal cord, wherein the proximal end of the needle is in electrical communication with a power supply and a controller;
- applying focused energy within the vocal cord at a pre-determined temperature is on the order of 70 degrees and a pre-determined period of time is about 30 seconds.

18. A system for performing a surgical procedure on an animal, comprising:
- a probe comprising a housing and a needle with an insulating body extending from the housing, the needle having a proximal end, and a first electrode at a distal end for insertion into the target tissue so that the electrode is substantially centered within a target tissue;
- a second electrode disposed in contact with the animal at a distance from the needle to create a circuit across the target tissue; and
- a power supply in electrical communication with the proximal end of the needle, the power supply having controls for applying focused energy within the target tissue by selecting two or more of a pre-determined power level, a pre-determined temperature ramp rate, a pre-determined temperature and a pre-determined period of time based on a thermal mass of the target tissue to form a heat plume within the target tissue to modify the target tissue by inducing one or more of cell necrosis, collagen shrinkage and scar formation without damage to tissue surrounding the target tissue.

19. The system of claim 18, wherein the needle has a temperature sensor disposed therein.

20. The system of claim 19, wherein the controls in the power supply include a control algorithm module configured to implement a feedback loop, the feedback loop capable of continually sensing a temperature or a resistance level and causing the controller to increase the temperature or the resistance level until a peak operating level is obtained in the target tissue of the animal.

21. The system of claim 20, wherein the controls in the power supply are further adapted to:
- activate the power supply and control to apply a short series of pilot power levels;
- measure a rate of temperature change associated with each pilot power level; and
- collect the measured rate of temperature change associated with each pilot power level to estimate the thermal mass and energy loss rate associated with the target tissue.

22. The system of claim 21, wherein the controls in the power supply are further adapted to calculate derivatives of the measured rate of temperature change to generate time-temperature curves.

23. The system of claim 18, wherein the energy is radio frequency energy.

24. The system of claim 18, wherein the second electrode comprises a second needle disposed at a fixed separation from the needle, wherein the fixed separation is selected based upon a desired volume of the heat plume to be generated within the target tissue.

* * * * *